US012672837B2

(12) United States Patent
Baumgart et al.

(10) Patent No.: US 12,672,837 B2
(45) Date of Patent: Jul. 7, 2026

(54) SYSTEM AND METHOD FOR ADJUSTMENT OF IMAGING COMPONENTS BASED ON OBJECT DETECTION

(71) Applicant: Canon Kabushiki Kaisha, Tokyo (JP)

(72) Inventors: John Baumgart, Vernon Hills, IL (US); Yi Hu, Vernon Hills, IL (US); Joseph Manak, Vernon Hills, IL (US); Haruki Iwai, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 434 days.

(21) Appl. No.: 18/316,283

(22) Filed: May 12, 2023

(65) Prior Publication Data

US 2024/0374230 A1 Nov. 14, 2024

(51) Int. Cl.
| | |
|---|---|
| *A61B 6/00* | (2024.01) |
| *A61B 6/04* | (2006.01) |
| *A61B 6/10* | (2006.01) |
| *G06T 7/00* | (2017.01) |
| *G06T 7/11* | (2017.01) |

(Continued)

(52) U.S. Cl.
CPC ............ *A61B 6/545* (2013.01); *A61B 6/0407* (2013.01); *A61B 6/102* (2013.01); *A61B 6/4441* (2013.01); *A61B 6/488* (2013.01); *G06T 7/0014* (2013.01); *G06T 7/11* (2017.01); *G06T 7/174* (2017.01); *A61B 6/12* (2013.01); *G06T 2207/10116* (2013.01); *G06T 2207/20081* (2013.01);

(Continued)

(58) Field of Classification Search
CPC ......... A61B 6/0407; A61B 6/102; A61B 6/12;

A61B 6/4441; A61B 6/488; A61B 6/545; G06T 2207/10116; G06T 2207/20081; G06T 2207/20084; G06T 2207/20224; G06T 2207/30004; G06T 7/0014; G06T 7/11; G06T 7/174; G06V 10/143; G06V 10/25; G06V 10/82
See application file for complete search history.

(56) References Cited

U.S. PATENT DOCUMENTS

| | | | |
|---|---|---|---|
| 5,906,578 A | 5/1999 | Rajan et al. | |
| 9,633,428 B2 * | 4/2017 | Simanovsky | ......... G06T 7/0006 |

FOREIGN PATENT DOCUMENTS

| | | |
|---|---|---|
| CN | 113274051 A | 8/2021 |
| CN | 114848019 A | 8/2022 |

OTHER PUBLICATIONS

Akbari et al. ; Robotic Ultrasound Scanning With Real-Time Image-Based Force Adjustment: Quick Response for Enabling Physical Distancing During the COVID-19 Pandemic ; frontiers in Robotics and AI, vol. 8 ; Mar. 22, 2021 ; 14 Pages.

* cited by examiner

*Primary Examiner* — Dani Fox
(74) *Attorney, Agent, or Firm* — Oblon, McClelland, Maier & Neustadt, L.L.P.

(57) ABSTRACT

A method of adjusting components in an imaging apparatus includes obtaining a first image, the first image being acquired by performing a scan using a first set of scan parameters; analyzing the first image to detect objects in the first image and corresponding features of the detected objects; based on a detection result of a first object having a corresponding first object feature in the first image, determining an action corresponding to the first object and the first object feature; determining an updated set of scan (Continued)

parameters based on the determined action; and controlling the imaging apparatus based on the updated set of scan parameters.

20 Claims, 9 Drawing Sheets

(51) Int. Cl.
    *G06T 7/174*            (2017.01)
    *A61B 6/12*            (2006.01)
(52) U.S. Cl.
    CPC ............... *G06T 2207/20084* (2013.01); *G06T 2207/20224* (2013.01); *G06T 2207/30004* (2013.01)

400

405 — Obtain image data

410 — Analyze image data

415 — Query database for potential reactions to analyzed image data

420 — Determine updated component parameters

425 — Adjust components based on updated component parameters

Fluoroscopy with Large FOV

Selecting Partial Area to Change the FOV

Enlarge the Image of the Partial Area

SYSTEM AND METHOD FOR ADJUSTMENT OF IMAGING COMPONENTS BASED ON OBJECT DETECTION

FIELD OF THE INVENTION

This disclosure relates to identifying and localizing an object and background region of interest, or a main region of interest, in an image generated by a fluoroscopy system. The imaging equipment is automatically adjusted for capturing the subsequent image.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

X-ray imaging systems and methods are widely used medical imaging tools for diagnosis and clinical interventions. Radiography systems are essential tools in interventional radiology procedures which may vary from a few minutes to several hours. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

In recent years, opportunities to perform surgery under X-ray fluoroscopy using an X-ray imaging apparatus have been increasing. The X-ray imaging apparatus can support the IVR (Interventional Radiology) surgery using the X-ray fluoroscopy. The IVR surgery using the X-ray fluoroscopy means mainly treatment using a catheter during the X-ray fluoroscopy. The X-ray imaging apparatus generates fluoroscopic images in chronological order and displays them in real time in IVR surgery using the X-ray fluoroscopy.

In both fluoroscopic mode and acquisition mode, a sequence of X-ray exposures is collected at a selected frame rate. During the procedure, the patient anatomy and the imaging geometry, such as Source-to-Imager Distance (SID) and angulation, may change frequently according to the radiologists' need.

In an interventional procedure using X-ray, there are several mechanical system components that may benefit from adjustment to either bring an object of interest into view or shield portions of a patient from unnecessary X-ray dose. These include the patient table and C-arm, X-ray attenuation filters, and X-ray collimation shutters. Currently, these items can be positioned or adjusted manually by someone operating the system, usually during fluoroscopy.

SUMMARY

The present disclosure relates to an imaging apparatus, including processing circuitry configured to obtain a first image, the first image being acquired by performing a scan using a first set of scan parameters, analyze the first image to detect objects in the first image and corresponding features of the detected objects, based on a detection result of a first object having a corresponding first object feature in the first image, determine an action corresponding to the first object and the first object feature, determine an updated set of scan parameters based on the determined action, and control the imaging apparatus based on the updated set of scan parameters.

The disclosure additionally relates to a method of adjusting components in an imaging apparatus, including obtaining a first image, the first image being acquired by performing a scan using a first set of scan parameters; analyzing the first image to detect objects in the first image and corresponding features of the detected objects; based on a detection result of a first object having a corresponding first object feature in the first image, determining an action corresponding to the first object and the first object feature; determining an updated set of scan parameters based on the determined action; and controlling the imaging apparatus based on the updated set of scan parameters.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION

Figure 1:
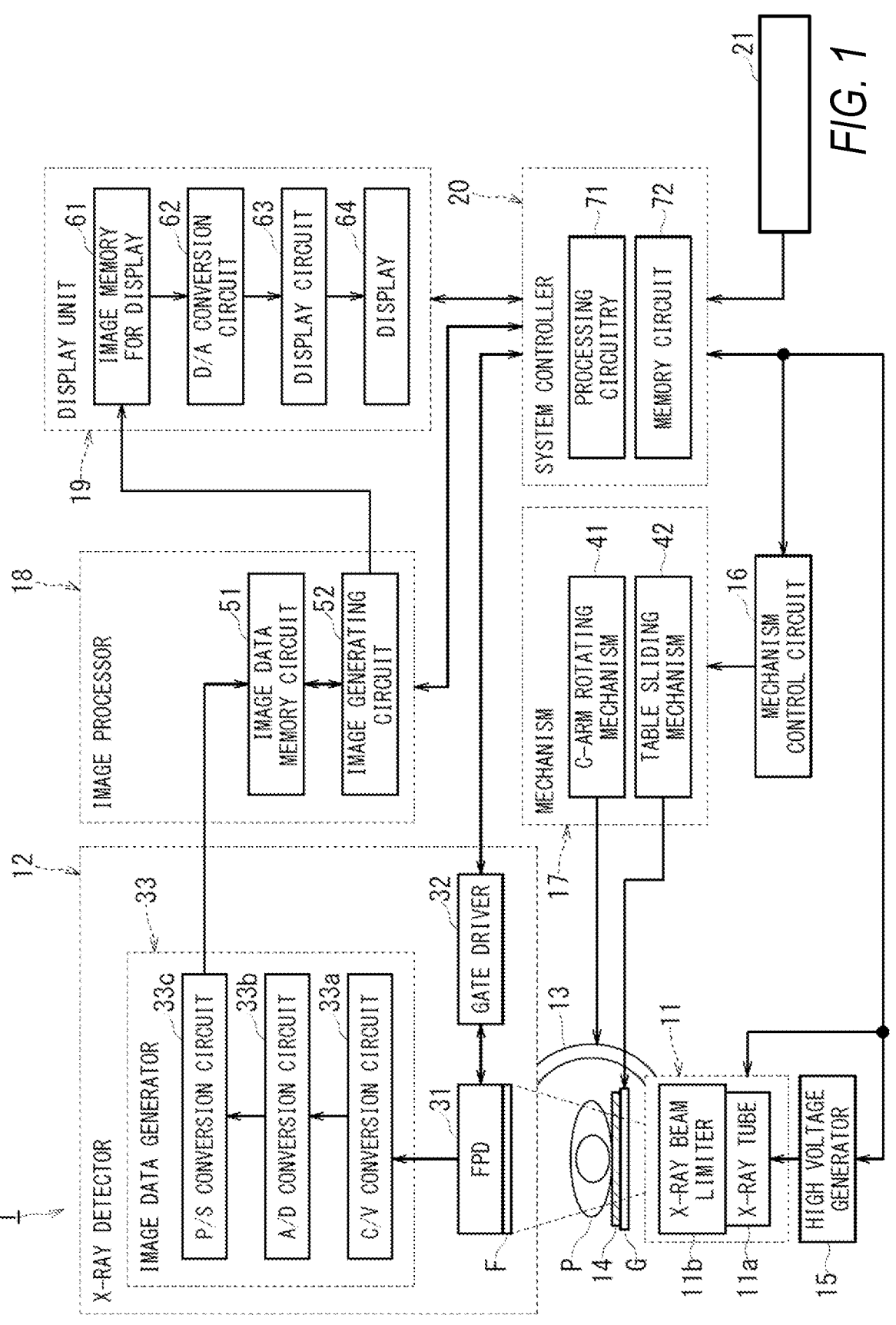
FIG. 1 is a schematic diagram showing a configuration of an X-ray imaging apparatus, according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Described herein is a system by which mechanical components of an X-ray imaging apparatus, including table, C-arm, x-ray collimators, attenuators, and filters, are automatically positioned in response to detected image content. Some systems can rely on system operators to manually position these components as devices are moved.

The X-ray imaging apparatus according to an embodiment includes an X-ray generator, an X-ray detector, an input interface, and processing circuitry. The X-ray generator is configured to generate X-rays. The X-ray detector is configured to detect the X-rays. The arm is configured to hold the X-ray generator and the X-ray detector. The input interface is configured to generate a direction signal for determining a rotating direction of the arm. The processing circuitry is configured to: display, on a display, an image based on the X-rays detected by the X-ray detector; control, based on a first control signal according to the direction signal, a rotating mechanism of the arm so that the arm performs a first rotation; and control, in response to an end of the first rotation, based on a second control signal, the rotating mechanism so that the arm performs a second rotation which returns the arm toward a position before the first rotation, the position being stored in a memory circuit.

FIG. 1 is a schematic diagram showing a configuration of an X-ray imaging apparatus according to an embodiment.

Figure 2:
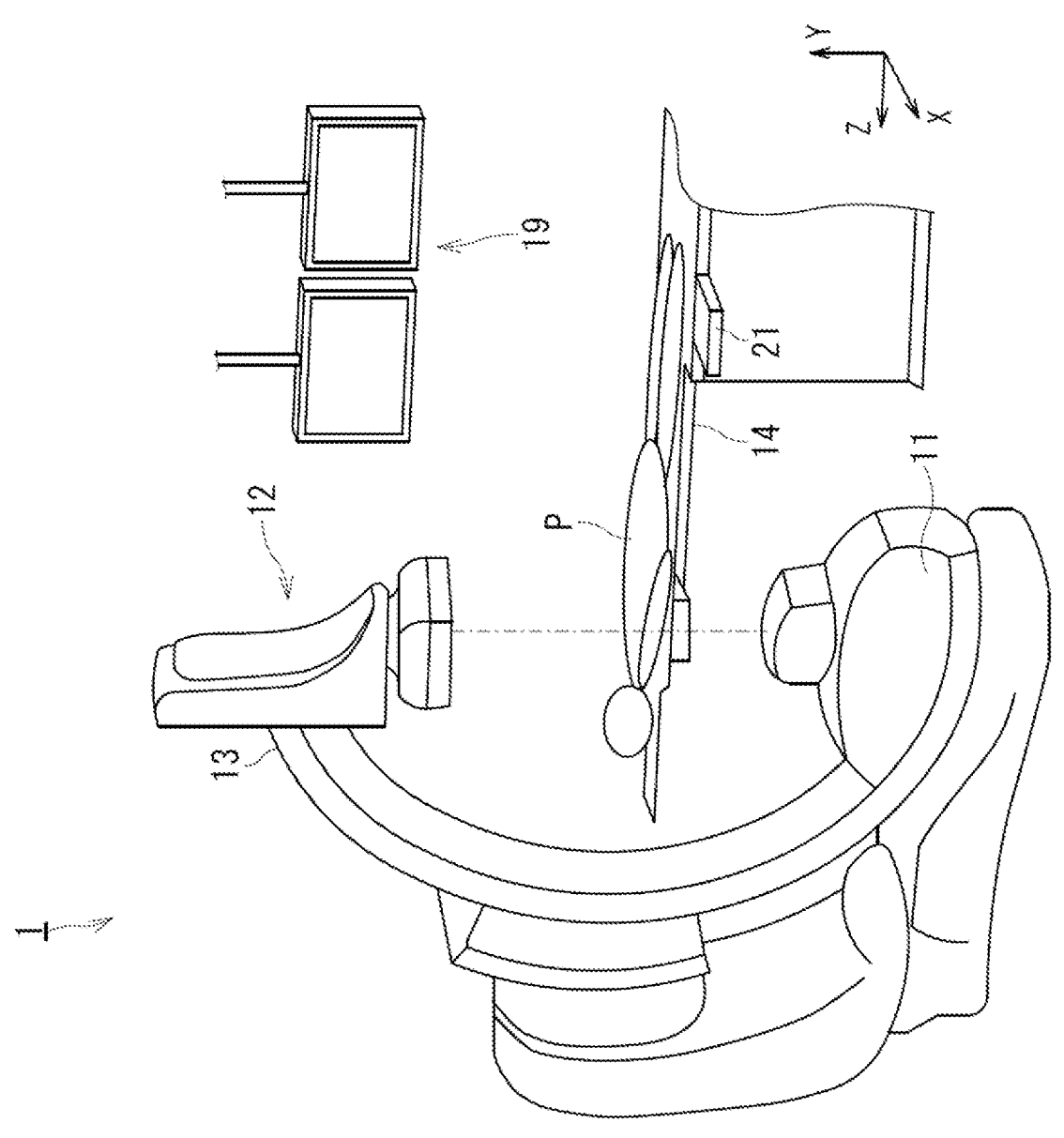
FIG. 2 is a perspective view showing an appearance of a part of the X-ray imaging apparatus, according to an embodiment of the present disclosure.

FIG. 2 is a perspective view showing an appearance of a part of the X-ray imaging apparatus according to the embodiment.

FIGS. 1 and 2 show an X-ray imaging apparatus 1 according to an embodiment. The X-ray imaging apparatus 1 is able to support the IVR surgery using X-ray fluoroscopy. The IVR surgery using the X-ray fluoroscopy means treatment using a catheter during the X-ray fluoroscopy. In the IVR surgery using the X-ray fluoroscopy, the X-ray imaging apparatus 1 generates fluoroscopic images in chronological order and displays them in real time.

The X-ray imaging apparatus 1 includes an X-ray generator 11, an X-ray detector 12, a C-arm 13, a table 14, a high voltage generator 15, a mechanism control circuit 16, a mechanism 17, an image processer 18, a display unit 19, and a first electronic device 20.

The X-ray generator 11 includes an X-ray tube 11a and an X-ray beam limiter 11b. The X-ray tube 11a irradiates, under the control of the first electronic device 20, a patient P with X-rays. The X-ray tube 11a is a vacuum tube for generating the X-rays. The X-ray tube 11a accelerates thermionic electrons emitted from a cathode (filament) by a high voltage applied between an anode and the cathode. Then, X-ray tube 11a generates the X-rays by causing the accelerated thermionic electrons to collide with the tungsten anode.

The X-ray beam limiter 11b controls, under the control of the first electronic device 20, sliding of diaphragms thereof, and forms an X-ray pyramid (cone beam) with respect to the X-rays emitted from the X-ray tube 11a. The X-ray beam limiter 11b is arranged between the X-ray tube 11a and the patient P. The X-ray beam limiter 11b narrows down the X-ray beam emitted from the X-ray tube 11a to a predetermined visual field size in order not to expose a part other than a target part of the patient P.

The X-ray detector 12 two-dimensionally detects, under the control of the first electronic device 20, the X-rays transmissive through the patient P. The X-ray detector 12 includes a flat panel detector (FPD) 31, a gate driver 32, and an image data generator 33.

The X-ray detector 12 includes a direct conversion system which directly converts the X-rays into electric charges, and an indirect conversion system which converts the X-rays into electric charges and then converts them into electric charges. In the embodiment, the former is described as an example, but the latter may be used.

The FPD 31 is an example of an X-ray detector configured by arranging minute elements two-dimensionally in the column and line directions. Each element of the FPD 31 includes an X-ray detecting element, a photoelectric film, a charge storage capacitor, and a thin film transistor (TFT). The X-ray detecting element senses the X-rays. The photoelectric film generates charges according to the incident X-ray dose. The charge storage capacitor accumulates the charges generated in the photoelectric film. The TFT reads the charges accumulated in the charge storage capacitor as raw data of an X-ray transmission image (fluoroscopic image or radiographic image) at a predetermined timing. It should be noted that the raw data of the X-ray fluoroscopic image may be converted using the non dosimeter dosimetry (NDD) method, and the surface dose data of the X-ray transmission image may be generated.

The gate driver 32 is installed to extract charges from the FPD 31. The image data generator 33 generates image data of an X-ray transmission image based on the raw data (or surface dose data) of the X-ray transmission image output from the X-ray detector 12.

The image data generator 33 includes a charge/voltage conversion circuit 33*a*, an analog to digital (A/D) conversion circuit 33*b*, and a parallel/serial conversion circuit 33*c*.

The charge/voltage conversion circuit 33*a* converts the electric charge read from the FPD 31 into a voltage. The A/D conversion circuit 33*b* converts the output of the charge/voltage conversion circuit 33*a* into digital signals. The parallel/serial conversion circuit 33*c* converts the digitally converted image data read in parallel on a line basis from the FPD 31 into serial signals.

In the X-ray imaging apparatus 1, in order to perform X-ray automatic exposure control, a photo pickup (for example, a fluorescent lighting type fiber detector) F may be incorporated in front of the FPD 31. In the case of X-ray examination for the X-ray fluoroscopy, X-rays for the X-ray fluoroscopy are detected by the FPD 31, and the feedback loop may be configured so that the luminance of the display 64 of the display unit 19 becomes constant, based on the detection signal. Alternatively, the feedback loop may be configured so that the average value of pixel signals (or video signals) imaged by the FPD 31 becomes constant.

In addition, in FIG. 1, the imaging system of the C-arm structure included in the X-ray imaging apparatus 1 shows a case where the X-ray generator 11 is an under table positioned below the table 14. However, it is not limited to that case. For example, the X-ray generator 11 may be an over table positioned above the table 14.

The C-arm 13 integrally holds the X-ray generator 11 and the X-ray detector 12. It should be noted that the arm holding the X-ray generator 11 and the X-ray detector 12 as one body is not limited to the so-called C-arm based on the "C" shape. For example, the arm integrally holding the X-ray generator 11 and the X-ray detector 12 may be a so-called Ω arm based on "Ω" shape.

The table 14 is able to place the patient P thereon.

The high voltage generator 15 supplies, under the control of the first electronic device 20, high voltage power to the X-ray tube 11*a*.

The mechanism control circuit 16 is a motor circuit for supplying, under the control of the first electronic device 20, electricity to the mechanism 17 to rotate the C-arm 13 or to slide the table 14.

The mechanism 17 includes a C-arm rotating mechanism 41 and a table sliding mechanism 42. The C-arm rotating mechanism 41 moves each motor unit constituting the C-arm rotating mechanism 41 under the control of the first electronic device 20 via the mechanism control circuit 16. Thus, the C-arm rotating mechanism 41 rotates the C-arm 13 holding the X-ray generator 11 and the X-ray detector 12 in a circular arc direction of the C-arm 13, or rotates the C-arm 13 holding the X-ray generator 11 and the X-ray detector 12 about a fulcrum of the C-arm 13.

The rotation of the C-arm 13 in the circular arc direction corresponds to a rotation in a direction of the cranial view (CRA) or a rotation in a direction of the caudal view (CAU). The rotation of the fulcrum center of the C-arm 13 corresponds to a rotation in a direction of the left anterior oblique view (LAO) or a rotation in a direction of the right anterior oblique view (RAO). It should be noted that the rotation of the C-arm 13 in the circular arc direction may have a configuration corresponding to the rotation in the direction of the LAO and the rotation in the direction of the RAO, and corresponding to the rotation of the direction of the CRA and the rotation of the direction of the CAU.

The table sliding mechanism 42 moves, under the control of the first electronic device 20 via the mechanism control circuit 16, each power unit constituting a table holder G which holds the table 14. Thus, the table sliding mechanism 42 is able to slide the table holder G in the left-right direction (the X-axis direction shown in FIG. 2 or the opposite direction), in the vertical direction (the Y-axis direction shown in FIG. 2 or the opposite direction), or in the body axis direction (the Z-axis direction shown in FIG. 2 or the opposite direction).

The image processor 18 includes an image data memory circuit 51 and an image generating circuit 52. The image data memory circuit 51 stores, under the control of the first electronic device 20, the image data sequentially output from the image data generator 33 line by line or frame unit.

Under the control of the first electronic device 20, the image generating circuit 52 performs image processing on the image data stored in the image data memory circuit 51, and records the image data after the image processing in the image data memory circuit 51. Examples of the image processing include enlargement/gradation/spatial filter processing of image data of X-ray transmission image, minimum value/maximum value tracing processing of image data accumulated in time series, subtraction processing, addition processing for removing noise, or the like.

The display unit 19 synthesizes, under the control of the first electronic device 20, data from text/graphic information such as X-ray emitting conditions and the like provided from the first electronic device 20 and from the image data of the X-ray transmission image processed by the image processor 18, and displays it. Specifically, the display unit 19 includes an image memory 61 for display, a digital to analog (D/A) converter 62, a display circuit 63, and a display 64.

The image memory 61 for display synthesizes data from the image data of the X-ray transmission image, and from the X-ray emitting conditions (tube voltage, tube current, fluoroscopic time, dose information, etc.) converted by the first electronic device 20, or from numerals and various characters which are incidental data of the image data, and temporarily records the synthesized data.

The D/A converter 62 converts the image data of the X-ray transmission image and the incidental data into analog signals.

The display circuit 63 is a circuit for format conversion for converting the analog signals into a TV format, thereby generating video signals.

The display 64 is a display device displaying the video signals, such as a liquid crystal display panel, a plasma display panel, an organic electro luminescence (EL) panel or the like.

The first electronic device 20 includes processing circuitry 71 and a memory circuit 72. The first electronic device 20 controls the entire X-ray imaging apparatus 1 according to an instruction of an operator input from the first electronic device 20. The first electronic device 20 performs control so as to perform an X-ray radiography for the purpose of generating an image used for diagnosis or the X-ray fluoroscopy with a reduced dose than the X-ray radiography. The X-ray fluoroscopy is roughly divided into a continuous fluoroscopy and a pulse fluoroscopy. The pulse fluoroscopy means a fluoroscopic method of intermittently emitting X-rays with intermittent rectangular waves unlike the continuous fluoroscopy. According to the pulse fluoroscopy, the continuity (frame rate) of fluoroscopic images is somewhat inferior to the continuous fluoroscopy, but the exposure dose to the patient can be suppressed compared to the continuous fluoroscopy.

The processing circuitry 71 is any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 71 achieves functions to be described later by reading out and executing a program stored in the memory circuit 72 or directly incorporated in the processing circuitry 71.

The processing circuitry 71 may be a single processing circuit or a combination of multiple processing circuit elements. In the latter case, the memory circuit 72 includes multiple memory elements each storing an element of a program that the processing circuitry 71 executes, and each corresponding to the processing circuit. Alternatively, in the latter case, the memory circuit 72 includes a single memory storing the program that the processing circuitry 71 executes, and corresponding to the multiple processing circuits.

The memory circuit 72 includes a semiconductor memory element such as a random access memory (RAM), a flash memory and the like, a hard disk, an optical disk and the like. The memory circuit 72 may be a portable media such as a universal serial bus (USB) memory, a digital video disk (DVD) and the like. The memory circuit 72 stores various processing programs (in addition to application programs, an operating system (OS) and the like are also included), data required for execution of the programs.

Figure 3:
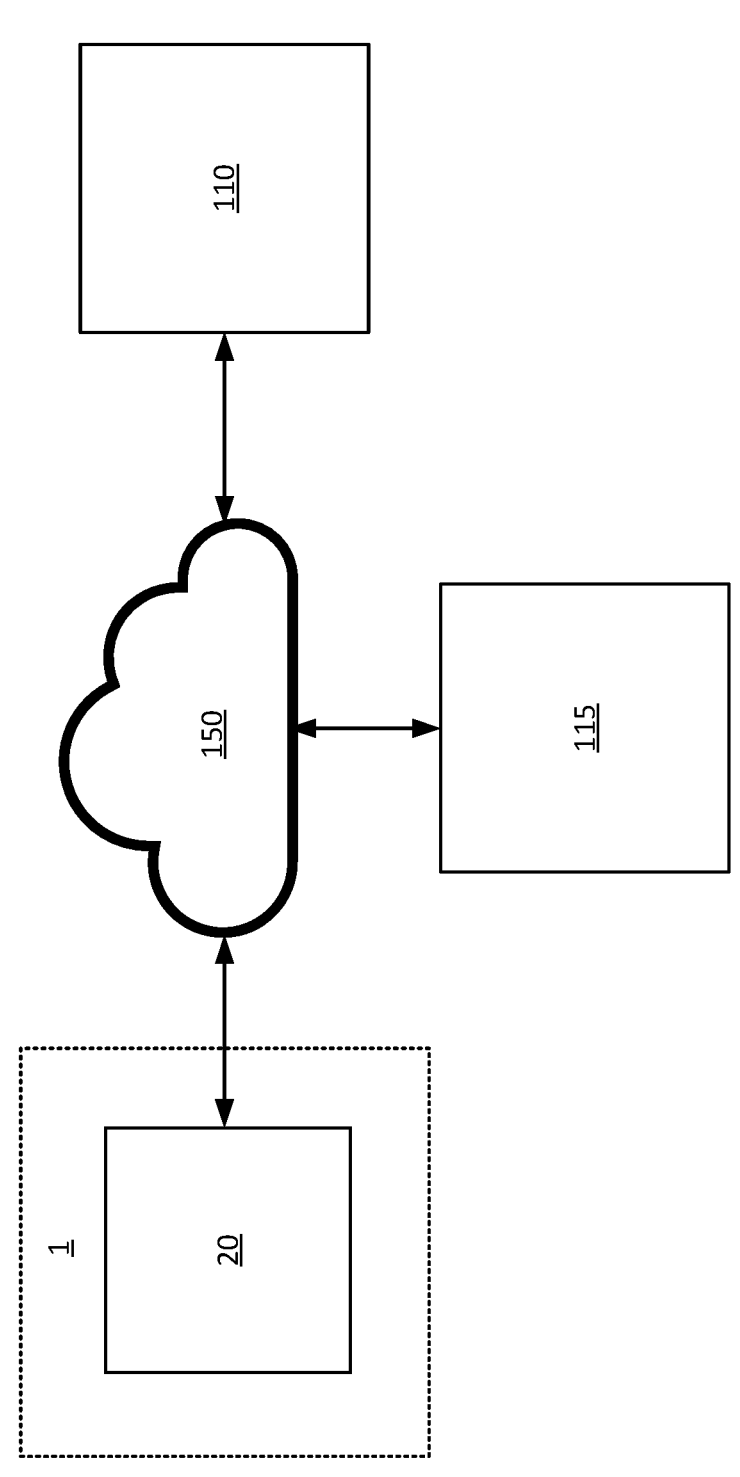
FIG. 3 is a schematic view of electronic devices communicatively connected to a server, according to an embodiment of the present disclosure.

FIG. 3 is a schematic view of the first electronic device 20, such as a client/user device communicatively connected, via a network 150, to a second electronic device 110, according to an embodiment of the present disclosure. In an embodiment, the first electronic device 20 can be communicatively connected to the second electronic device 110, such as a server, via a network 150. A third electronic device 115 can be communicatively connected to the first electronic device 20 and the second electronic device 110. The devices can be connected via a wired or a wireless connection. The connection between, for example, the first electronic device 20 and the second electronic device 110 can be via the network 150, wherein the network 150 is wireless. In an embodiment, the first electronic device 20 can be configured to obtain data from the operator (of the first electronic device 20). Notably, the first electronic device 20 can transmit the data over the communication network 150 to the networked second electronic device 110 and/or the third electronic device 115.

In an embodiment, the first electronic device 20 need not be communicatively coupled to the other device or the network 150. That is, the method described herein can be run entirely on the first electronic device 20 using the obtained imaging data.

An application can be installed or accessible on the first electronic device 20 for executing the methods described herein. The application may also be integrated into the operating system (OS) of the first electronic device 20. The first electronic device 20 can be any electronic device such as, but not limited to, a personal computer, a tablet pc, a smart-phone, a smart-watch, an integrated AR/VR (Augmented Reality/Virtual Reality) headwear with the necessary computing and computer vision components installed (e.g., a central processing unit (CPU), a graphics processing unit (GPU), integrated graphics on the CPU, etc.), a smart-television, an interactive screen, a smart projector or a projected platform, an IoT (Internet of things) device or the like.

In an embodiment, the X-ray imaging apparatus 1 can be configured to detect objects within an acquired image, including patient anatomy, implanted devices such as pacemakers, artificial joints, and dental work, as well as interventional devices such as catheters, catheter tips, guide wires, angioplasty balloons, and electrophysiology (EP) leads, among others. The X-ray imaging apparatus 1 can be configured to use the location, motion, and previous location of detected objects to automatically make mechanical adjustments, including moving the patient table or C-arm to bring the object into an advantageous position in the field of view, X-ray attenuation filters to reduce X-ray exposure to over-exposed anatomy, and X-ray collimation shutters to block X-rays from reaching anatomy that is not necessary for the procedure.

Furthermore, the X-ray imaging apparatus 1 can use information provided by the operator about the exam being performed, such as anatomy being examined and devices to be used. To avoid collisions among system components or motion beyond physical limits, current component positionings can be used to determine motion paths.

Figure 4:
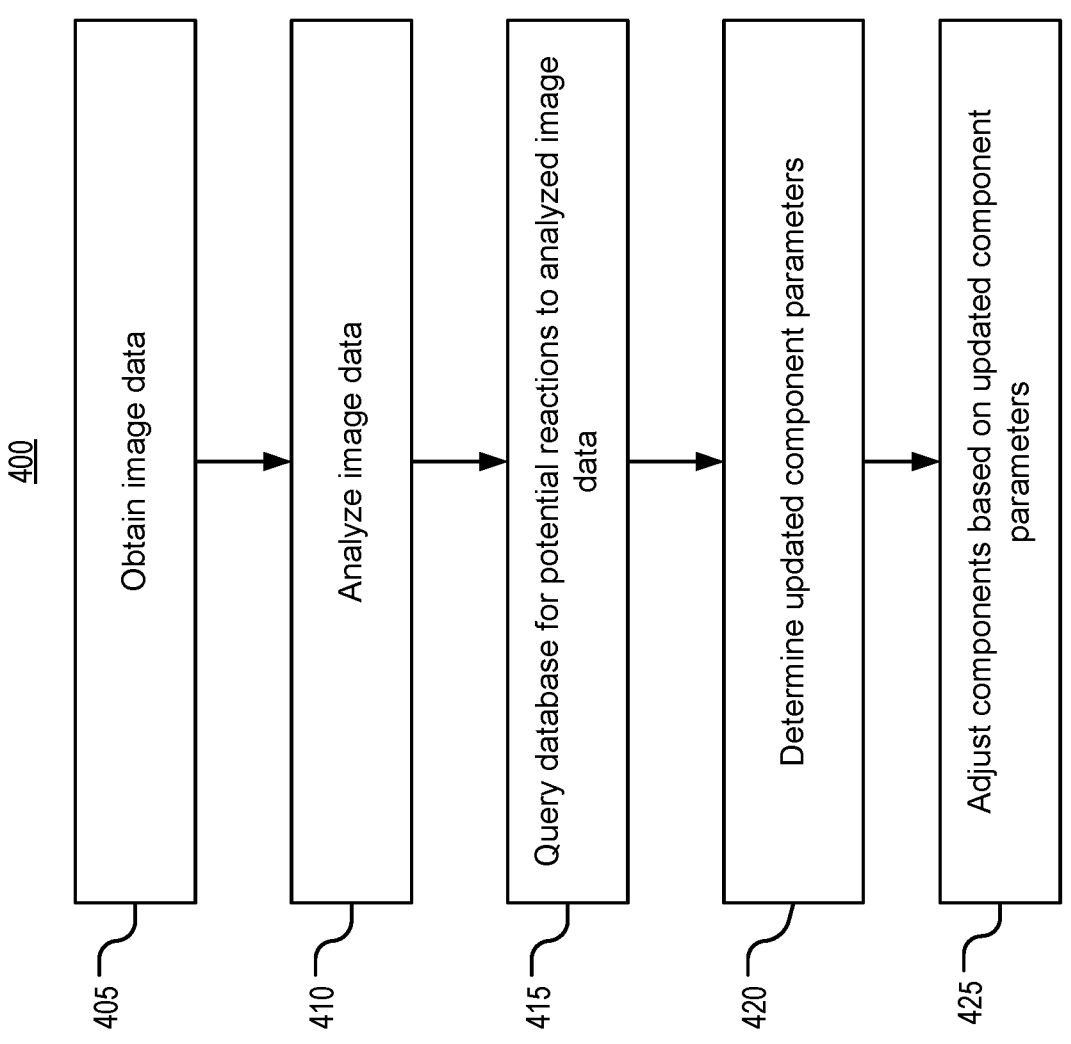
FIG. 4 shows a non-limiting example of a flow chart for a method of determining and applying optimized component parameters, according to an embodiment of the present disclosure.

To this end, FIG. 4 shows a non-limiting example of a flow chart for a method 400 of determining and applying optimized component parameters, according to an embodiment of the present disclosure. In one embodiment, step 405 includes obtaining image data using the X-ray imaging apparatus 1.

In an embodiment, step 410 includes analyzing the image data obtained from the X-ray imaging apparatus 1. Analysis of the image data can include identifying objects of interest.

In an embodiment, step 415 includes querying a database of system or apparatus actions for appropriate reactions to the analyzed image data.

In an embodiment, step 420 includes determining updated parameters for the components of the X-ray imaging apparatus 1.

In an embodiment, step 425 includes adjusting the components of the X-ray imaging apparatus 1 based on the determined updated parameters for the components.

In an embodiment, with reference to step 405 and step 410, a neural network can be used to segment the obtained image data from the X-ray imaging apparatus 1 and identify an object or multiple objects of interest. For example, the identified object can be a catheter tip. Further, the identified object can be described based on the object's appearance and movement. For example, the identified catheter tip can be determined to be in motion. The motion can be determined by, for example, comparing a previously analyzed image to a current image and determining a position change for the object of interest. For example, the identified object can be a lung field and the appearance of the lung field can be described as bright.

In an embodiment, with reference to step 415 and step 420, the database of apparatus actions can include identified objects, object descriptions, and corresponding suggested actions (appropriate reactions) based on the identified objects and the object descriptions. Moreover, as additional images are analyzed and actions performed, the identified objects, object descriptions, and suggested actions can be further correlated with one another. Based on the database information and the analyzed image data, the updated parameters can be determined for each of the components in the X-ray imaging apparatus 1.

In an embodiment, with reference to step 425, the determined updated parameters can be used to adjust the X-ray imaging apparatus 1. For example, the first electronic device 20 can adjust the high voltage power to the X-ray tube 11a via the high voltage generator 15, the electricity to the C-arm rotating mechanism 41 to rotate the C-arm 13 via the mechanism control circuit 16, the electricity to the table sliding mechanism 42 to adjust the table 14, and/or the FPD 31 via the gate driver 32. Upon receiving the respective adjustments from the first electronic device 20, the final positions of the components can be realized. The adjustments can also include compensation for predetermined component range of motion, optimal path to the updated positions in the event of potential collisions, and optimal combination of component adjustments to achieve the entire adjustment in the least amount of time.

Table 1 describes an example of various objects, object descriptions and appearances, and the corresponding action performed. Notably, the objects, object descriptions, and object appearances can be collectively described as a scene.

In an embodiment, step 515 includes receiving apparatus and patient parameters.

In an embodiment, step 520 includes querying a database of system or apparatus actions for appropriate reactions to the analyzed image data.

In an embodiment, step 525 includes determining updated parameters for the components of the X-ray imaging apparatus 1.

In an embodiment, step 530 includes adjusting the components of the X-ray imaging apparatus 1 based on the determined updated parameters for the components.

Notably, step 505 and step 510 of method 500 are similar to step 405 and step 410 of method 400.

TABLE 1

Examples of identified objects and object descriptions,
defined rules/actions, and corresponding priorities.

| Scene Description Parameters | | | Actions | | | |
|---|---|---|---|---|---|---|
| Object | Motion | Apperance | Positioning | Attenuator | Collimator | Priority |
| Catheter Tip | In motion | | Follow object | | | 10 |
| Catheter Tip - Left Heart | Stationary | | Position at upper left | | | 20 |
| Catheter Tip - Right Heart | Stationary | | Position at uppercenter | | | 20 |
| Lung Field | | Bright | | Cover object | | 50 |
| EP Catheter | | | Center | | Collimate outside electrodes | 15 |

As seen in Table 1, a priority score or value can also be assigned to each object and corresponding action to generate an order of execution or adjustment for each component. For example, the identified lung field can be assigned a high priority (e.g., 50) in order to quickly cover the identified lung with an attenuator in order to attenuate or reduce the radiation that the lung is being exposed to. For example, adjusting the components to follow the catheter tip can be assigned a lower priority (e.g., 10) since this has a lower immediate impact on the health of the patient and can be adjusted last.

Figure 5:
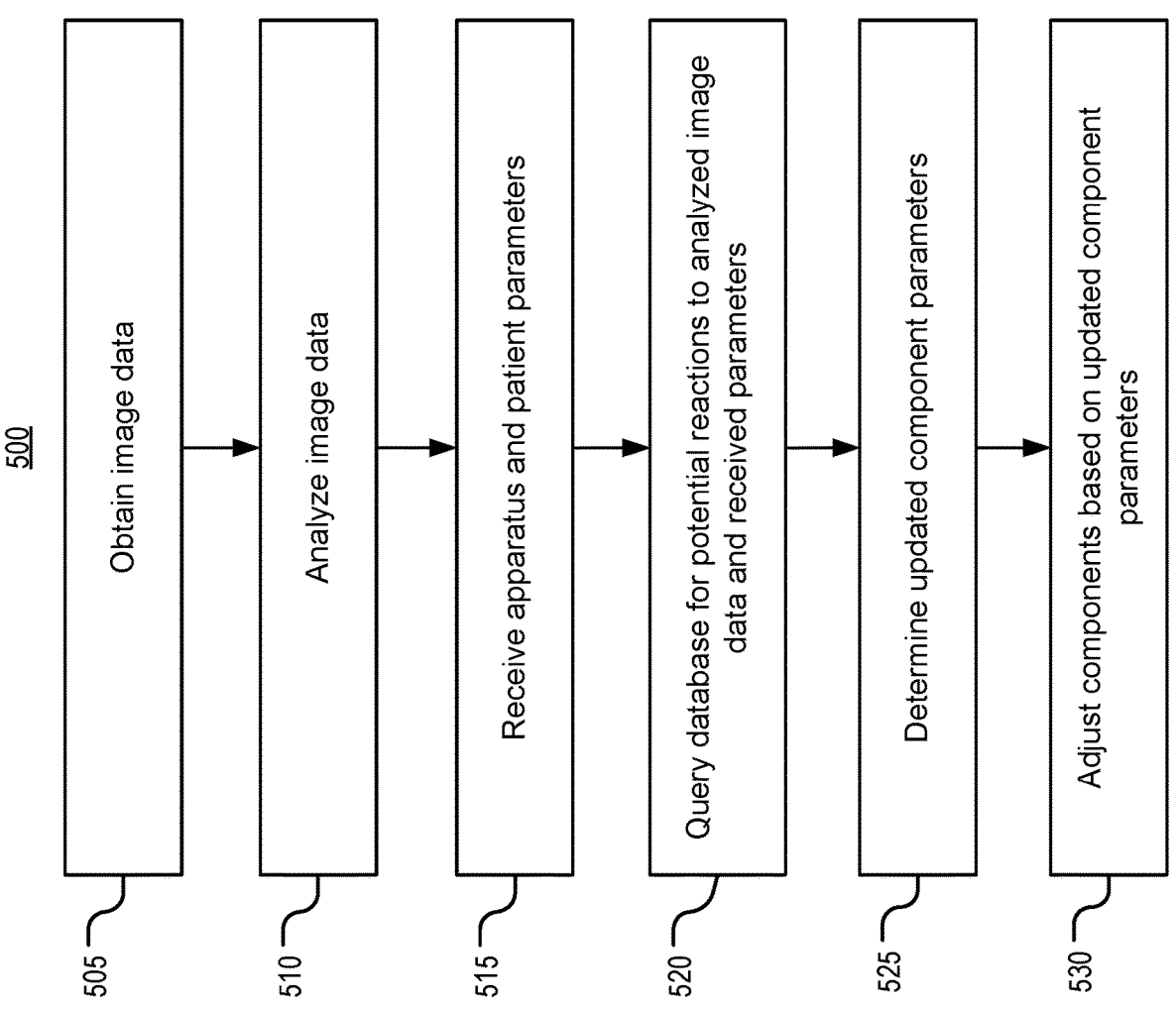
FIG. 5 shows a non-limiting example of a flow chart for a method of determining and applying optimized component parameters, according to an embodiment of the present disclosure.

In an embodiment, the X-ray imaging apparatus 1 can be further assisted or guided by receiving a priori knowledge or predetermined known scan parameters related to the type of exam being performed. To this end, FIG. 5 shows a non-limiting example of a flow chart for a method 500 of determining and applying optimized component parameters, according to an embodiment of the present disclosure.

In an embodiment, step 505 includes obtaining image data using the X-ray imaging apparatus 1.

In an embodiment, step 510 includes analyzing the image data obtained from the X-ray imaging apparatus 1. Analysis of the image data can include identifying objects of interest.

In an embodiment, with reference to step 515, step 520, and step 525, the database of apparatus actions can include identified objects, object descriptions, exam types, and corresponding suggested actions (appropriate reactions) based on the identified objects, the object descriptions, and the exam types. Notably, the exam type can be known before the scan is performed and provided as an additional known input. This can increase the efficiency of the image analysis as well as the accuracy of the determined actions and adjustment of the X-ray imaging apparatus 1 because an object recognition step can be eliminated and replaced with known information. Additionally or alternatively, the image analysis to identify objects in the image can still be performed in order to confirm the provided known scan parameters. Based on the database information, the analyzed image data, and the provided known scan parameters, the updated parameters can be determined for each of the components in the X-ray imaging apparatus 1.

Notably, step 530 of method 500 is similar to step 425 of method 400.

Table 1 describes an example of various objects, object descriptions and appearances, and the corresponding action performed. Notably, the objects, object descriptions, and object appearances can be collectively described as a scene.

TABLE 2

Examples of identified objects and object descriptions, known scan
parameters, defined rules/actions, and corresponding priorities.

| Scene Description Parameters | | | Exam | Actions | | | |
|---|---|---|---|---|---|---|---|
| Object | Motion | Appearance | Type | Positioning | Attenuator | Collimator | Priority |
| Catheter Tip | In motion | | | Follow object | | | 10 |
| Catheter Tip | Stationary | | Left Heart | Position at upper left | | | 20 |

TABLE 2-continued

Examples of identified objects and object descriptions, known scan
parameters, defined rules/actions, and corresponding priorities.

| | Scene Description Parameters | | Exam | | Actions | | |
|---|---|---|---|---|---|---|---|
| Object | Motion | Appearance | Type | Positioning | Attenuator | Collimator | Priority |
| Catheter Tip | Stationary | | Right Heart | Position at uppercenter | | | 20 |
| Lung Field | | Bright | | | Cover object | | 50 |
| EP Catheter | | | | Center | | Collimate outside electrodes | 15 |

As seen in Table 2, an additional column for provided input related to the scan or exam is included. For example, the left heart catheter tip previously identified by the X-ray imaging apparatus 1 during the image analysis step can be provided by the operator manually in the "exam type" column. As shown, the exam type can be provided for one of the catheter tip objects as a left heart exam, while the exam type can be provided for another of the catheter tip objects as a right heart exam. As previously described, this can allow for skipping some object detection time and reducing the processing power needed, as well as increasing the accuracy of the resulting adjustment determinations (or reducing the number of conflicts for objects detected). For example, for the left heart catheter tip, since the exam type has been input by the operator, the adjustment needed can automatically be determined because there is no uncertainty regarding the current procedure being performed. As such, the adjustment can be to position the catheter tip at the upper left of the scan field in order to optimize the viewing of a guide wire that will be eventually inserted into the left coronary arteries and become visible.

Notably, there can occasionally be multiple actions or adjustments that can provide the same desired image. However, there can be a best or better option among the multiple adjustments available. For example, a software-based image processing can be a superior option in certain instances compared to moving the entire table 14 in order to follow or track a detected object in the analyzed image. As shown in Table 3, a new priority can be assigned, such as an action or adjustment priority. Therefore, tracking the catheter tip in motion can be performed preferably using software (ifluoro) instead of moving the entire table 14, which is highlighted via the higher action priority of 70 for the software option compared to the lower action priority of 30 for the physical relocation of the patient.

TABLE 3

Examples objects with the same scene priority
but different action priorities.

| Object | Motion | Scene Priority | Actions | Action Priority |
|---|---|---|---|---|
| Catheter Tip | in motion | 50 | ifluoro to follow an object | 70 |
| Catheter Tip | in motion | 50 | move table to follow an object | 30 |

Figure 6:
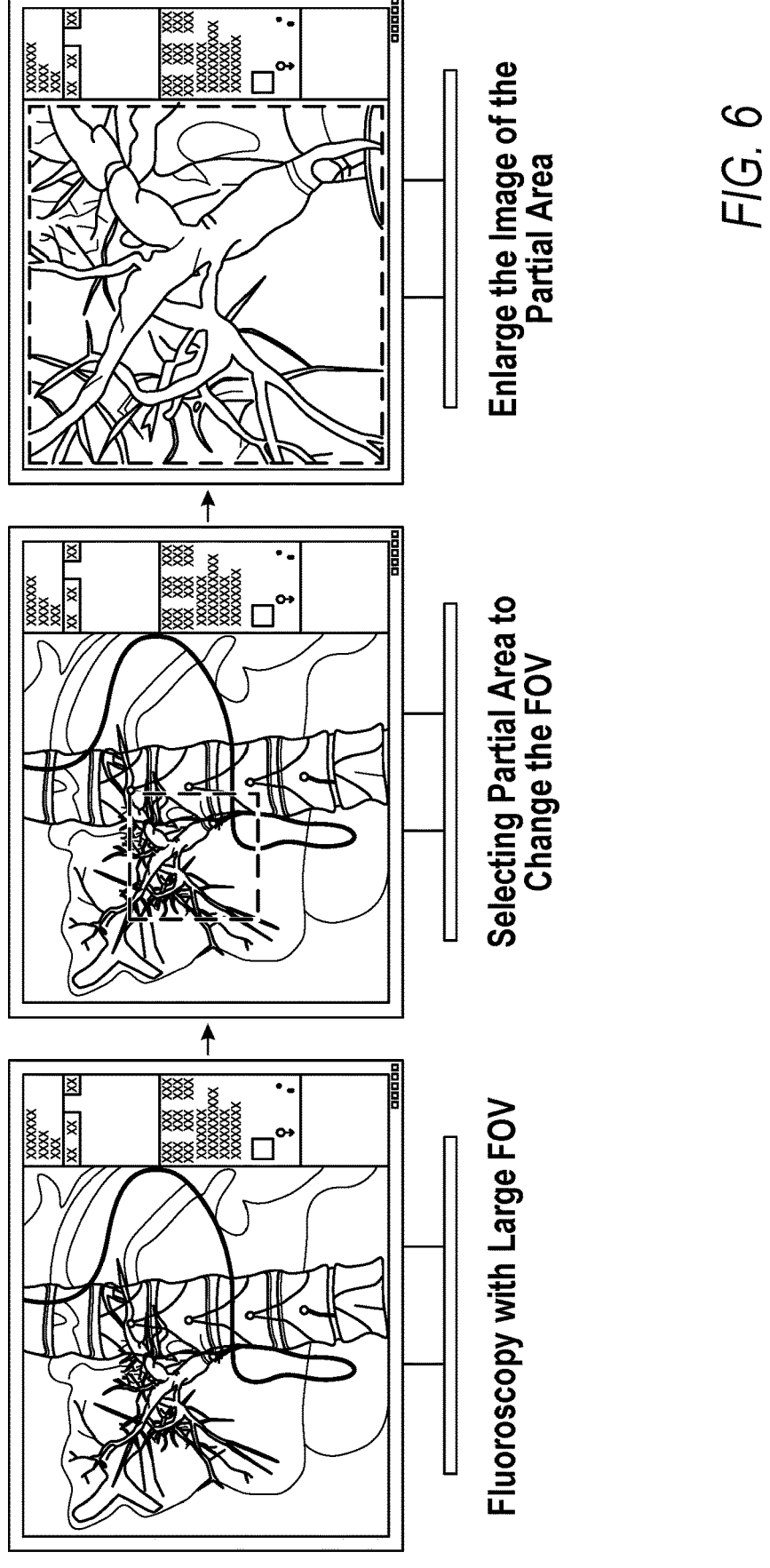
FIG. 6 is a schematic of an example object and adjusted using software, according to an embodiment of the present disclosure.

FIG. 6 is a schematic of an example object and adjusted using software, according to an embodiment of the present disclosure. In an embodiment, the detected object of interest can be imaged using fluoroscopy with a large field of view (FOV) on the left. The operator can desire to view the detected object of interest, which can be accomplished by taking another scan or more simply by performing a software adjustment. As shown in the center image, the object of interest can be zoomed in by selecting (via software) a partial area (encompassed by the white square) to change the FOV. On the right, the partial area image has been enlarged. A similar operation can be performed for other adjustments, such as brightness, contrast, etc. This provides an advantage over changing the X-ray dose and performing another scan. Of course, changing the X-ray dose can be a superior option in other conditions. For example, the catheter and a vessel can be detected, and the catheter can be inserted into the bifurcation region of the vessel. Here, the better adjustment can be to change the X-ray conditions than to use an image processing (software).

Notably, the rules or actions for adjusting the X-ray imaging apparatus 1 above based on the database information can be hard-coded or strictly set. This can be programmed before the scan is performed to set the actions, corresponding priorities, etc. In doing so, conflicts between component adjustments can be resolved using the pre-set rules. Additionally or alternatively, a manual over-ride by the operator can be performed to adjust the rules, such as altering an order of adjustment even though the corresponding assigned priority can dictate another order.

Figure 7:
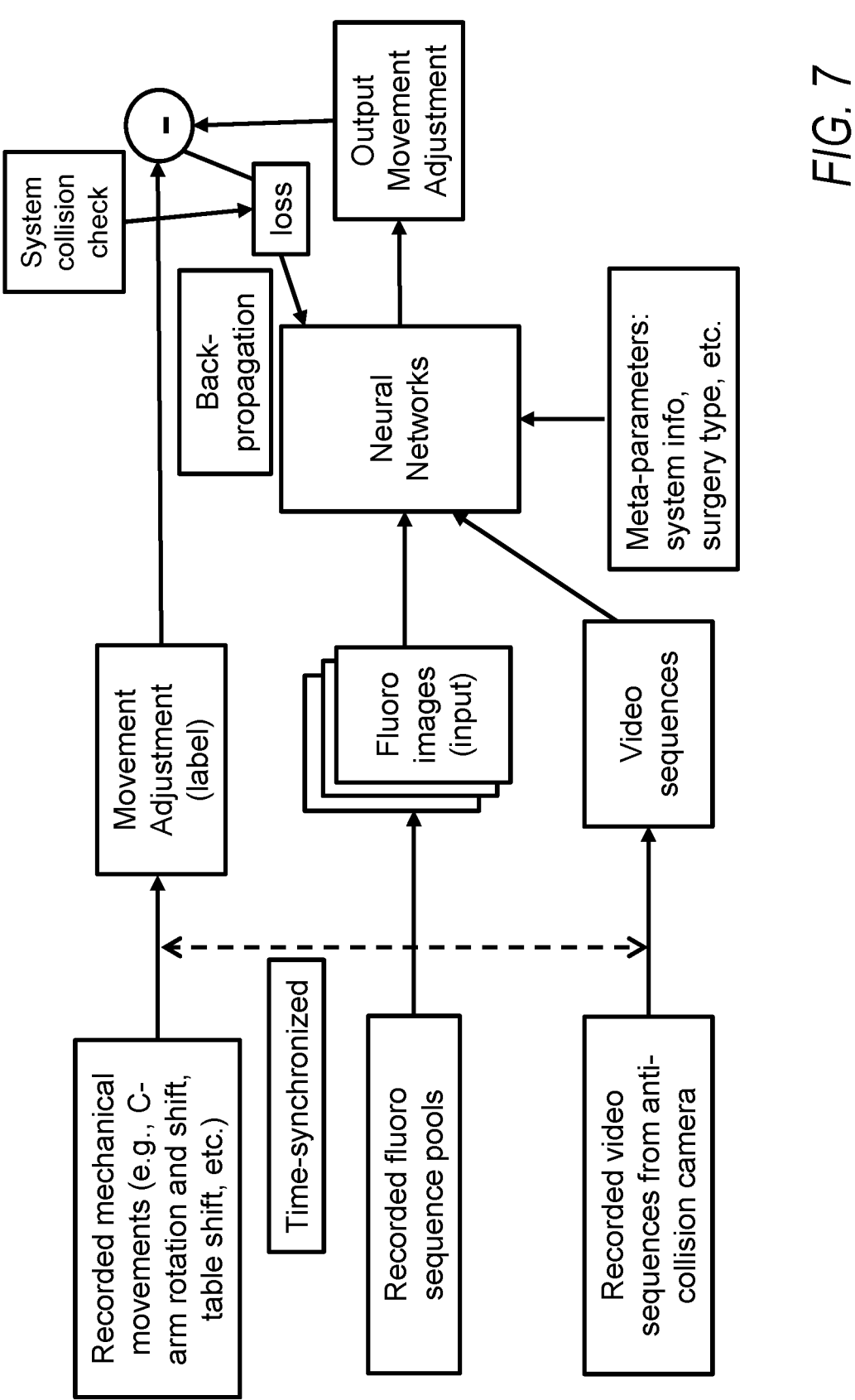
FIG. 7 is a schematic of a workflow for training the end-to-end neural network for adjusting the X-ray imaging apparatus, according to an embodiment of the present disclosure.

In an embodiment, a trained neural network can be used to control the X-ray imaging apparatus 1. To this end, FIG. 7 is a schematic of a workflow for training the end-to-end neural network for adjusting the X-ray imaging apparatus 1, according to an embodiment of the present disclosure. Training input for the neural network can include recorded and time-synchronized mechanical movements of the components and fluoroscopy image sequences and images or videos from an anti-collision camera 21 included as part of the X-ray imaging apparatus 1. The anti-collision camera 21 can be configured to obtain and record image or video data during the scan. In particular, the anti-collision camera 21 can be focused primarily on recording video data of the components that move during the adjustment. For example, the anti-collision camera 21 is an optical camera capable of obtaining image or video data in the visible wavelength spectrum. For example, the anti-collision camera 21 is a light detection and ranging (LIDAR) camera configured to generate a point cloud (or 3D scan) of object location information using a pulsed laser to measure ranges. For example, the anti-collision camera 21 is a Radar device configured to determine object distances using electromagnetic radiation in the radio or microwave regime. For example, the anti-collision camera 21 is an ultrasonic sensor configured to determine object distances using sound waves.

Furthermore, more than one of the anti-collision camera 21 can be included in the X-ray imaging apparatus 1. For example, multiple assorted anti-collision cameras 21 can be aimed at different parts of the X-ray imaging apparatus 1 and configured to obtain image or video data related to physical proximity of various items or components around the X-ray imaging apparatus 1 and the imaging environment. For example, the X-ray imaging apparatus 1 can include two of the anti-collision camera 21 to form a stereo pair of optical cameras capable of acquiring depth information. For example, the X-ray imaging apparatus 1 can include one or more optical cameras, plus one or more LIDAR cameras, plus one or more Radar devices.

In an embodiment, while the input image sequences can include at least two frames, better training can be achieved using more frames. Furthermore, a regularization term can be used in a loss function to avoid system collisions. As shown, recorded fluoroscopy sequence pools can be parsed to generate the fluoroscopy images that can be used as training input for the neural network. This can help train the X-ray imaging apparatus 1 to detect and label or describe objects of interest more accurately, as well as determine the appropriate adjustment more accurately for the detected and labeled object of interest. Additionally, recorded video sequences acquired by the anti-collision camera 21 can be parsed to generate video sequences that can be used as training input for the neural network. This can help train the X-ray imaging apparatus 1 to optimize movement paths for the components of the X-ray imaging apparatus 1 that will be relocated. The previously described a priori information can also be used as an training input for the neural network. That is, the exam type, the known objects of interest, the object descriptions, the corresponding adjustments, etc. can be input as known, ground-truth parameters to help train the neural network. Notably, the recorded and mechanical movements, fluoroscopy image sequences, and videos from anti-collision camera can be time-synchronized when input into the neural network as the training input. Further, the recorded mechanical movements, such as that of the C-arm 13, the table 14, etc., can be labeled with a corresponding adjustment or action.

In an embodiment, the neural network trained on the various training inputs can be configured to generate, as an output, a movement adjustment or multiple movement adjustments to optimize the X-ray imaging apparatus 1 during subsequent scans and image acquisitions. As previously mentioned, the regularization term can be used in a loss function to avoid system collisions and input back into the neural network as additional training data.

Figure 8A:
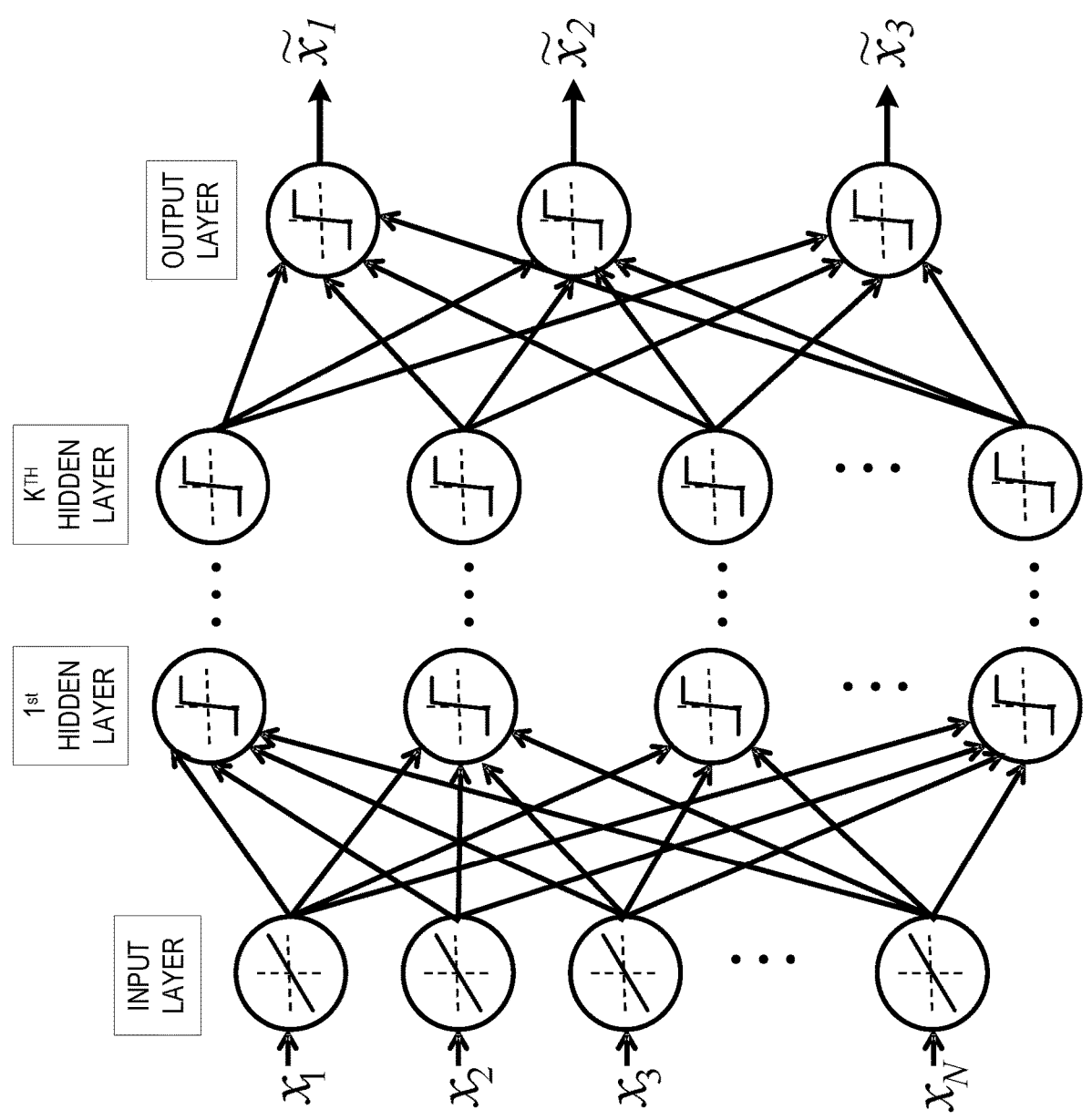
FIG. 8A shows an example of a general artificial neural network (ANN) having N inputs, K hidden layers, and three outputs, according to an embodiment of the present disclosure.
Figure 8B:
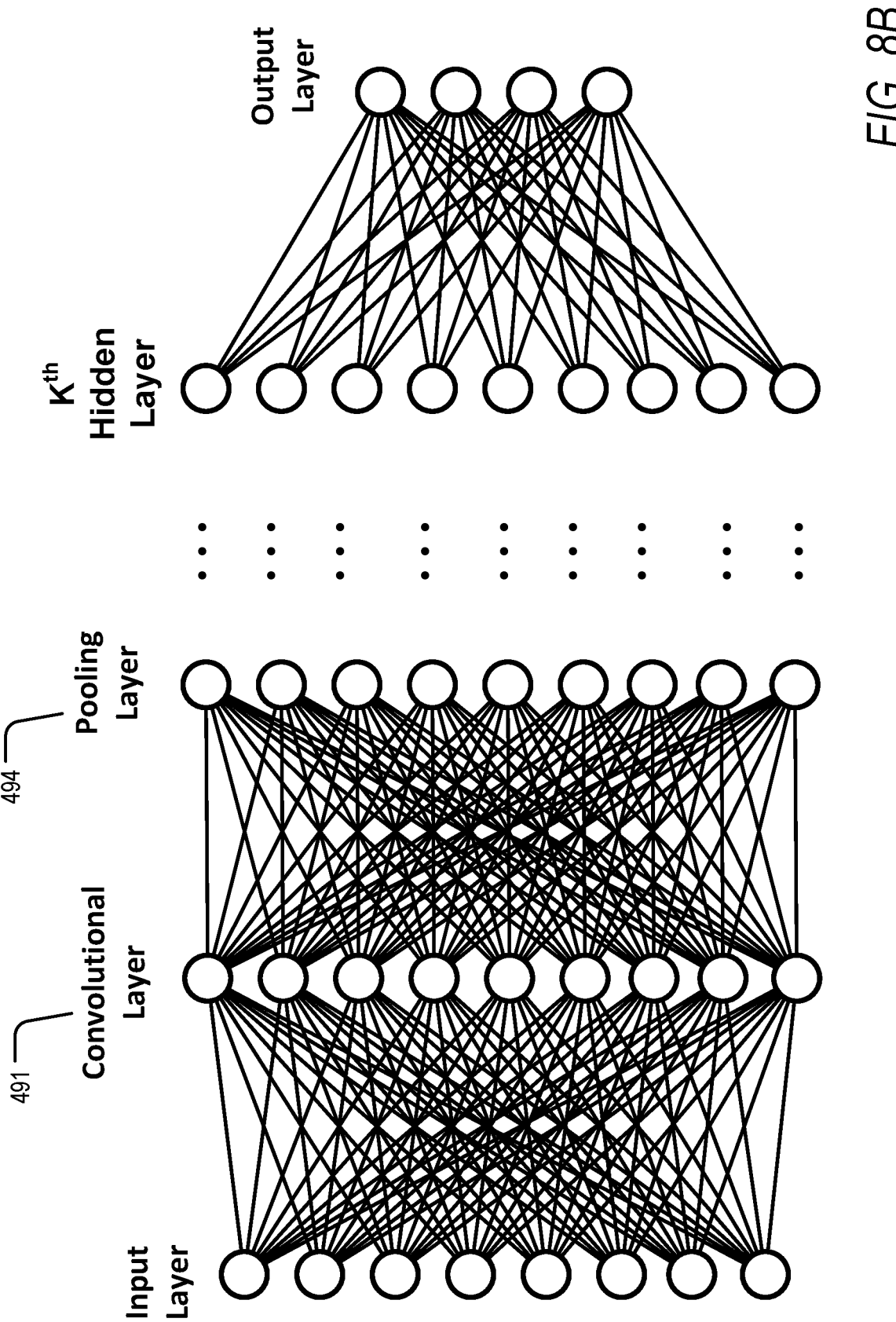
FIG. 8B shows a non-limiting example of a convolutional neural network (CNN), as in the present disclosure.

FIG. 8A and FIG. 8B show examples of the inter-connections between layers in a convolutional neural network (CNN), according to an embodiment of the present disclosure. In an embodiment, the CNN can include fully connected, convolutional, pooling, batch normalization, and activation layers, all of which are explained above and below. In certain preferred implementations of the CNN, convolutional layers are placed close to the input layer, whereas fully connected layers, which perform the high-level reasoning, are placed further down the architecture towards the loss function. Pooling layers can be inserted after convolutions and provide a reduction lowering the spatial extent of the filters, and thus the amount of learnable parameters. Batch normalization layers regulate gradient distractions to outliers and accelerate the learning process. Activation functions are also incorporated into various layers to introduce nonlinearity and enable the network to learn complex predictive relationships. The activation function can be a saturating activation function (e.g., a sigmoid or hyperbolic tangent activation function) or rectified activation function.

FIG. 8A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The CNN of the present disclosure can have more than three layers of neurons and have as many output neurons $\hat{x}_N$ as input neurons, wherein N is the number of, for example, pixels in the training image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can be further defined as a composition of other functions. This can be conveniently represented as a network structure, with arrows depicting the dependencies between variables, as shown in FIG. 8A and FIG. 8B. For example, the ANN can use a nonlinear weighted sum, wherein $m(x)=K(\Sigma_i w_i n_i(x))$ and where K (commonly referred to as the activation function) is some predefined function, such as the hyperbolic tangent.

In FIG. 8A (and similarly in FIG. 8B), the neurons (i.e., nodes) are depicted by circles around a threshold function. For the non-limiting example shown in FIG. 8A, the inputs are depicted as circles around a linear function and the arrows indicate directed communications between neurons. In certain implementations, the CNN is a feedforward network.

The CNN of the present disclosure operates to achieve a specific task by searching within the class of functions F to learn, using a set of observations, to find $m^* \in F$, which solves the specific task in some optimal sense. For example, in certain implementations, this can be achieved by defining a cost function C: F→m such that, for the optimal solution $m^*$, $C(m^*) \leq C(m) \forall m \in F$ (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 8B shows a non-limiting example of a convolutional neural network (CNN), as in the present disclosure. CNNs are a type of ANN that have beneficial properties for image processing and, therefore, have special relevancy for applications of image processing. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap to obtain a better representation of the original image. This processing pattern can be repeated over multiple layers having convolution 491 and pooling layers 494, as shown, and can include batch normalization and activation layers.

As generally applied above, following after a convolution layer 491, a CNN can include local and/or global pooling layers 494 which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolution layers, which means that the same filter (weights bank) is used as the coefficients for each pixel in the layer, both reducing memory footprint and improving performance. Compared to other image processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be as set forth in the following parentheticals.

(1) An imaging apparatus, comprising processing circuitry configured to obtain a first image, the first image being acquired by performing a scan using a first set of scan parameters, analyze the first image to detect objects in the first image and corresponding features of the detected objects, based on a detection result of a first object having a corresponding first object feature in the first image, determine an action corresponding to the first object and the first object feature, determine an updated set of scan parameters based on the determined action, and control the imaging apparatus based on the updated set of scan parameters.

(2) The apparatus of (1), wherein the processing circuitry is further configured to: receive information of a known object and a corresponding known feature of the known object, and determine the action based on a combination of the received information and the detection result.

(3) The apparatus of either (2) or (3), wherein the processing circuitry is further configured to: obtain a second image, the second image being acquired by performing a scan using a second set of scan parameters, analyze the second image to detect the first object and the first object feature in the second image, determine whether there is a difference in the first object feature between the first image and the second image, upon determining that there is a difference in the first object feature between the first image and the second image, generate an updated first object feature, and determine an updated action corresponding to the first object and the updated first object feature from a database.

(4) The apparatus of any one of (1) to (3), wherein the processing circuitry is further configured to: determine a second updated set of scan parameters based on the determined updated action, and control the imaging apparatus based on the second updated set of scan parameters.

(5) The apparatus of any one of (1) to (4), wherein the first object and the first object feature are identified using machine vision.

(6) The apparatus of any one of (2) to (5), wherein the processing circuitry is further configured to determine the action corresponding to the first object and the first object feature by applying information of the first object and the first object feature to a trained machine learning model.

(7) The apparatus of (6), wherein the trained machine learning model includes a neural network trained on reference known objects, reference known object features, and corresponding reference actions corresponding to the reference known objects and the reference known object features.

(8) The apparatus of any one of (2) to (7), wherein the received information received by the processing circuitry is examination settings for the scan.

(9) The apparatus of any one of (1) to (8), wherein the processing circuitry is further configured to train a neural network to directly determine the action corresponding to the first object and the first object feature based on input of the first image to the neural network.

(10) The apparatus of any one of (1) to (9), wherein, in performing the analyzing of the first image to detect objects in the first image, the processing circuitry is further configured to use a trained neural network to segment the first image and detect the objects in the first image and the corresponding first object feature.

(11) The apparatus of any one of (1) to (10), wherein the imaging apparatus further comprises a table, an X-ray source configured to generate X-rays, an X-ray detector configured to detect the X-rays, an arm configured to hold the X-ray source and the X-ray detector, and an optical camera configured to obtain video data of the table, the X-ray source, the X-ray detector, and the arm, and the processing circuitry is further configured to adjust at least two of the table, the X-ray source, the X-ray detector, and the arm simultaneously based on the updated set of scan parameters and the obtained video data, the at least two of the table, the X-ray source, the X-ray detector, and the arm avoiding a collision by the simultaneous adjustment based on the obtained video data

(12) A method of adjusting components in an imaging apparatus, comprising: obtaining a first image, the first image being acquired by performing a scan using a first set of scan parameters; analyzing the first image to detect objects in the first image and corresponding features of the detected objects; based on a detection result of a first object having a corresponding first object feature in the first image, determining an action corresponding to the first object and the first object feature; determining an updated set of scan parameters based on the determined action; and controlling the imaging apparatus based on the updated set of scan parameters.

(13) The method of (12), further comprising receiving information of a known object and a corresponding known feature of the known object; and determining the action based on a combination of the received information and the detection result.

(14) The method of either (12) or (13), further comprising obtaining a second image, the second image being acquired by performing a scan using a second set of scan parameters; analyzing the second image to detect the first object and the first object feature in the second image; determining whether there is a difference in the first object feature between the first image and the second image; upon determining that there is a difference in the first object feature between the first image and the second image, generating an updated first object feature; and determining an updated action corresponding to the first object and the updated first object feature from a database.

(15) The method of any one of (12) to (14), further comprising: determining a second updated set of scan parameters based on the determined updated action; and controlling the imaging apparatus based on the second updated set of scan parameters.

(16) The method of any one of (12) to (15), wherein the first object and the first object feature are identified using machine vision.

(17) The method of any one of (13) to (16), further comprising determining the action corresponding to the first object and the first object feature by applying information of the first object and the first object feature to a trained machine learning model.

(18) The method of (17), wherein the trained machine learning model includes a neural network trained on reference known objects, reference known object features, and corresponding reference actions corresponding to the reference known objects and the reference known object features.

(19) The method of any one of (12) to (18), wherein the imaging apparatus further includes a table, an X-ray source configured to generate X-rays, an X-ray detector configured to detect the X-rays, an arm configured to hold the X-ray source and the X-ray detector, and an optical camera configured to obtain video data of the table, the X-ray source, the X-ray detector, and the arm, and the method further comprises adjusting at least two of the table, the X-ray source, the X-ray detector, and the arm simultaneously based on the updated set of scan parameters and the obtained video data, the at least two of the table, the X-ray source, the X-ray detector, and the arm avoiding a collision by the simultaneous adjustment based on the obtained video data.

(20) A non-transitory computer-readable storage medium including executable instructions, which when executed by circuitry, cause the circuitry to perform a method of adjusting components in an imaging apparatus, comprising obtaining a first image, the first image being acquired by performing a scan using a first set of scan parameters; analyzing the first image to detect objects in the first image and corresponding features of the detected objects; based on a detection result of a first object having a corresponding first object feature in the first image, determining an action corresponding to the first object and the first object feature; determining an updated set of scan parameters based on the determined action; and controlling the imaging apparatus based on the updated set of scan parameters.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed is:

1. An imaging apparatus, comprising:
   processing circuitry configured to
      obtain a first medical image, the first medical image being acquired by performing a scan using a first set of scan parameters,
      analyze the first medical image to detect a plurality of objects in the first medical image and corresponding features of the detected plurality of objects,
      determine an action corresponding to a combination of a first object and a first object feature, which has a relatively high priority among a plurality of combinations of objects and object features detected in the first medical image,
      determine an updated set of scan parameters based on the determined action, and
      control the imaging apparatus based on the updated set of scan parameters.

2. The imaging apparatus of claim 1, wherein the processing circuitry is further configured to:
   receive information of a known object and a corresponding known feature of the known object, and
   determine the action based on a combination of the received information and the detection result.

3. The imaging apparatus of claim 1, wherein the processing circuitry is further configured to:
   obtain a second medical image, the second medical image being acquired by performing a scan using a second set of scan parameters,
   analyze the second medical image to detect the first object and the first object feature in the second medical image,
   determine whether there is a difference in the first object feature between the first medical image and the second medical image,
   upon determining that there is a difference in the first object feature between the first medical image and the second medical image, generate an updated first object feature, and
   determine an updated action corresponding to the first object and the updated first object feature from a database.

4. The imaging apparatus of claim 3, wherein the processing circuitry is further configured to:
   determine a second updated set of scan parameters based on the determined updated action, and
   control the imaging apparatus based on the second updated set of scan parameters.

5. The imaging apparatus of claim 1, wherein the first object and the first object feature are identified using machine vision.

6. The imaging apparatus of claim 2, wherein the processing circuitry is further configured to determine the action corresponding to the first object and the first object feature by applying information of the first object and the first object feature to a trained machine learning model.

7. The imaging apparatus of claim 6, wherein the trained machine learning model includes a neural network trained on reference known objects, reference known object features, and corresponding reference actions corresponding to the reference known objects and the reference known object features.

8. The imaging apparatus of claim 2, wherein the received information received by the processing circuitry is examination settings for the scan.

9. The imaging apparatus of claim 1, wherein the processing circuitry is further configured to train a neural network to directly determine the action corresponding to the first object and the first object feature based on input of the first medical image to the neural network.

10. The imaging apparatus of claim 1, wherein, in performing the analyzing of the first medical image to detect objects in the first medical image, the processing circuitry is further configured to use a trained neural network to segment the first medical image and detect the objects in the first medical image and the corresponding first object feature.

11. The imaging apparatus of claim 1, wherein
the imaging apparatus further comprises a table, an X-ray source configured to generate X-rays, an X-ray detector configured to detect the X-rays, an arm configured to hold the X-ray source and the X-ray detector, and an optical camera configured to obtain video data of the table, the X-ray source, the X-ray detector, and the arm, and
the processing circuitry is further configured to adjust at least two of the table, the X-ray source, the X-ray detector, and the arm simultaneously based on the updated set of scan parameters and the obtained video data, the at least two of the table, the X-ray source, the X-ray detector, and the arm avoiding a collision by the simultaneous adjustment based on the obtained video data.

12. A method of adjusting components in an imaging apparatus, comprising:
obtaining a first medical image, the first medical image being acquired by performing a scan using a first set of scan parameters;
analyzing the first medical image to detect a plurality of objects in the first medical image and corresponding features of the detected plurality of objects;
determining an action corresponding to a combination of a first object and a first object feature, which has a relatively high priority among a plurality of combinations of objects and object features detected in the first medical image;
determining an updated set of scan parameters based on the determined action; and
controlling the imaging apparatus based on the updated set of scan parameters.

13. The method of claim 12, further comprising:
receiving information of a known object and a corresponding known feature of the known object; and
determining the action based on a combination of the received information and the detection result.

14. The method of claim 12, further comprising:
obtaining a second medical image, the second medical image being acquired by performing a scan using a second set of scan parameters;

analyzing the second medical image to detect the first object and the first object feature in the second medical image;
determining whether there is a difference in the first object feature between the first medical image and the second medical image;
upon determining that there is a difference in the first object feature between the first medical image and the second medical image, generating an updated first object feature; and
determining an updated action corresponding to the first object and the updated first object feature from a database.

15. The method of claim 14, further comprising:
determining a second updated set of scan parameters based on the determined updated action; and
controlling the imaging apparatus based on the second updated set of scan parameters.

16. The method of claim 12, wherein the first object and the first object feature are identified using machine vision.

17. The method of claim 13, further comprising determining the action corresponding to the first object and the first object feature by applying information of the first object and the first object feature to a trained machine learning model.

18. The method of claim 17, wherein the trained machine learning model includes a neural network trained on reference known objects, reference known object features, and corresponding reference actions corresponding to the reference known objects and the reference known object features.

19. The method of claim 12, wherein
the imaging apparatus further includes a table, an X-ray source configured to generate X-rays, an X-ray detector configured to detect the X-rays, an arm configured to hold the X-ray source and the X-ray detector, and an optical camera configured to obtain video data of the table, the X-ray source, the X-ray detector, and the arm, and
the method further comprises adjusting at least two of the table, the X-ray source, the X-ray detector, and the arm simultaneously based on the updated set of scan parameters and the obtained video data, the at least two of the table, the X-ray source, the X-ray detector, and the arm avoiding a collision by the simultaneous adjustment based on the obtained video data.

20. A non-transitory computer-readable storage medium including executable instructions, which when executed by circuitry, cause the circuitry to perform a method of adjusting components in an imaging apparatus, comprising:
obtaining a first medical image, the first medical image being acquired by performing a scan using a first set of scan parameters;
analyzing the first medical image to detect a plurality of objects in the first medical image and corresponding features of the detected plurality of objects;
determining an action corresponding to a combination of a first object and a first object feature, which has a relatively high priority among a plurality of combinations of objects and object features detected in the first medical image;
determining an updated set of scan parameters based on the determined action; and
controlling the imaging apparatus based on the updated set of scan parameters.

* * * * *